United States Patent
Prakash et al.

(10) Patent No.: US 11,419,677 B2
(45) Date of Patent: Aug. 23, 2022

(54) HIGH-EFFICIENCY, DIRECTIONAL MICROWAVE ABLATION ANTENNA

(71) Applicant: Kansas State University Research Foundation, Manhattan, KS (US)

(72) Inventors: Punit Prakash, Manhattan, KS (US); Brogan McWilliams, Minneapolis, MN (US); Emily Frederick, Roeland Park, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 512 days.

(21) Appl. No.: 15/532,449

(22) PCT Filed: Dec. 1, 2015

(86) PCT No.: PCT/US2015/063210
§ 371 (c)(1),
(2) Date: Jun. 1, 2017

(87) PCT Pub. No.: WO2016/089887
PCT Pub. Date: Jun. 9, 2016

(65) Prior Publication Data
US 2017/0265940 A1    Sep. 21, 2017

Related U.S. Application Data

(60) Provisional application No. 62/086,507, filed on Dec. 2, 2014.

(51) Int. Cl.
*A61B 18/18*    (2006.01)
*A61B 17/00*    (2006.01)
*A61B 18/00*    (2006.01)

(52) U.S. Cl.
CPC .... *A61B 18/1815* (2013.01); *A61B 17/00234* (2013.01); *A61B 2017/00318* (2013.01);
(Continued)

(58) Field of Classification Search
CPC ........ A61B 18/1815; A61B 2018/0057; A61B 2018/183; A61B 2018/00005;
(Continued)

(56) References Cited

U.S. PATENT DOCUMENTS

| 4,204,549 A | 5/1980 | Paglione |
| 4,643,186 A * | 2/1987 | Rosen .................... A61B 17/22 606/159 |

(Continued)

OTHER PUBLICATIONS

International Search Report and Written Opinion dated Feb. 26, 2016, in PCT/US15/63210, filed Dec. 1, 2015.

*Primary Examiner* — Linda C Dvorak
*Assistant Examiner* — Bradford C. Blaise
(74) *Attorney, Agent, or Firm* — Hovey Williams LLP

(57) ABSTRACT

An electrosurgical device (10) operable to deliver microwave energy to cause targeted tissue ablation is provided. The electrosurgical device (10) comprises an antenna (26), a reflector (30), and a dielectric material (34) disposed therebetween. The selection of the dielectric material (30) and the relative positioning of the antenna (26) and the reflector (30) provide impedance matching between the antenna (26) and a transmission line (12) so as to minimize heating along the length of the device (10) during use.

17 Claims, 7 Drawing Sheets

(52) U.S. Cl.
CPC .......... *A61B 2018/005* (2013.01); *A61B 2018/00023* (2013.01); *A61B 2018/00488* (2013.01); *A61B 2018/00494* (2013.01); *A61B 2018/00511* (2013.01); *A61B 2018/00517* (2013.01); *A61B 2018/00541* (2013.01); *A61B 2018/00577* (2013.01); *A61B 2018/00809* (2013.01); *A61B 2018/00904* (2013.01); *A61B 2018/00982* (2013.01); *A61B 2018/1838* (2013.01); *A61B 2018/1846* (2013.01); *A61B 2018/1853* (2013.01); *A61B 2018/1861* (2013.01); *A61B 2018/1869* (2013.01)

(58) Field of Classification Search
CPC .......... A61B 2018/00011; A61B 2018/00023; A61B 2018/1823; A61B 2018/1838; A61B 2018/1846; A61B 2018/1853; A61B 2018/1861; A61B 2018/1869; A61B 2018/1876; A61B 2018/1884; A61B 2018/1892
See application file for complete search history.

(56) References Cited

U.S. PATENT DOCUMENTS

| | | | | |
|---|---|---|---|---|
| 6,245,062 | B1* | 6/2001 | Berube | A61B 18/14 606/33 |
| 6,287,302 | B1* | 9/2001 | Berube | A61B 18/18 606/33 |
| 6,471,696 | B1* | 10/2002 | Berube | A61B 18/1492 606/33 |
| 6,673,068 | B1* | 1/2004 | Berube | A61B 5/042 600/374 |
| 2002/0193786 | A1 | 12/2002 | Berube et al. | |
| 2003/0083654 | A1* | 5/2003 | Chin | A61B 18/1492 606/41 |
| 2003/0163128 | A1* | 8/2003 | Patil | A61B 5/0538 606/41 |
| 2005/0245920 | A1 | 11/2005 | Vitullo et al. | |
| 2005/0273090 | A1* | 12/2005 | Nieman | A61B 18/14 606/15 |
| 2008/0071259 | A1 | 3/2008 | Gauthier et al. | |
| 2011/0077633 | A1* | 3/2011 | Bonn | A61B 18/1815 606/33 |
| 2011/0077634 | A1* | 3/2011 | Brannan | A61B 18/18 606/33 |
| 2011/0213353 | A1* | 9/2011 | Lee | A61B 18/1815 606/33 |
| 2011/0238053 | A1* | 9/2011 | Brannan | A61B 17/3211 606/33 |
| 2012/0004651 | A1* | 1/2012 | Shiu | A61B 18/1815 606/33 |
| 2012/0110834 | A1 | 5/2012 | Smith et al. | |
| 2012/0123403 | A1* | 5/2012 | Brannan | A61B 18/1815 606/33 |
| 2014/0012250 | A1 | 1/2014 | Willyard | |
| 2017/0252106 | A1* | 9/2017 | Brannan | A61B 18/1815 |
| 2018/0256251 | A1* | 9/2018 | Hagness | A61B 18/1815 |
| 2018/0261922 | A1* | 9/2018 | Behdad | A61B 18/1815 |

* cited by examiner

HIGH-EFFICIENCY, DIRECTIONAL MICROWAVE ABLATION ANTENNA

RELATED APPLICATIONS

This is a national stage application under 35 U.S.C. § 371 of International Patent Application No. PCT/US2015/063210, filed Dec. 2, 2015, which claims the benefit of U.S. Provisional Application No. 62/086,507, filed Dec. 2, 2014, which is incorporated by reference herein in its entirety.

BACKGROUND OF THE INVENTION

Field of the Invention

The present invention is generally directed toward an electrosurgical device operable to deliver microwave energy of sufficient intensity so as to cause targeted ablation of tissue located within a human or animal body. The electrosurgical device exhibits excellent impedance matching between the antenna and microwave energy transmission line due to the selection of an appropriate dielectric material positioned between the antenna and the reflector and the relative distance between the antenna and reflector.

Description of the Prior Art

Microwave ablation (MWA) is an increasingly used thermal therapy modality for minimally-invasive treatment of tumors and benign disease. Other energy sources for thermal ablation include radiofrequency current, lasers, catheter-based ultrasound applicators, chemical, and cryoablation. These procedures may be performed minimally invasively, typically under guidance of ultrasound, or computerized tomography guidance, or under open surgery. MWA has found clinical applications in the treatment of tumors in the liver, kidney, lung, and bone, as well for treatment of cardiac arrhythmias, ablation of benign prostate tissue to treat hyperplasia (BPH), ablation of the uterine endometrial lining to treat menorrhagia, ablation of the esophageal wall for treating Barrett's esophagus and GERD, ablation of nerves for treating back pain, and ablation of renal nerves for treating chronic high blood pressure.

During an ablation procedure, an antenna is inserted into the target tissue, and radiates electromagnetic energy at microwave frequencies; most currently available devices operate within frequency bands approved for industrial, scientific, and medical (ISM) use, centered at 915 MHz and 2.45 GHz. Electromagnetic energy radiated from the antenna is deposited in the electromagnetic lossy tissue leading to heating via dielectric hysteresis. While thermal damage following ablation is a complex function of the time-temperature history during heating, temperatures in excess of 60° C. lead to near-instantaneous cell death by coagulative necrosis. Irreversible, but not lethal, thermal damage may occur in cells heated above 42° C. A fundamental principal of successful ablation is the creation of an ablation zone that sufficiently covers the entire tumor while providing a margin of safety for adjacent tissues.

In most microwave ablation procedures, the antenna is inserted into the center of the targeted tissue, and the ablation zone grows radially outward. When ablating targets in proximity to critical structures, caution must be taken to ensure complete thermal coverage of the target volume, while precluding thermal damage to non-targeted tissues. Fluid installation between the target site and organs at risk of injury has emerged as a practical technique for minimizing heating of non-targeted tissues. Conventional microwave ablation antennas are based on coaxial antenna designs, have axially symmetric radiation patterns, and do not offer control of the energy deposition pattern in the angular expanse. Spatial control of the energy deposition pattern is limited to control of heating along the antenna length, achieved by employing a sleeve/choke. While multiple antennas operated as a phased-array may offer some limited steering of power deposition, the increased invasiveness and system complexity are drawbacks compared to the use of single applicators.

The following references are illustrative of the state of the art with respect to microwave ablation devices: U.S. Pat. Nos. 5,314,466, 6,245,062, 6,312,427, 6,383,182, 6,471,696, 7,115,126, and 8,235,981.

SUMMARY OF THE INVENTION

According to one embodiment of the present invention there is provided an electrosurgical device for tissue ablation. The device generally comprises a transmission line for transmitting an electromagnetic signal from a signal generator, an antenna coupled to the transmission line and configured for emitting electromagnetic energy therefrom sufficiently strong to cause tissue ablation, and a reflector positioned laterally from the antenna. The device further comprises a first dielectric material surrounding the antenna and disposed between the antenna and reflector. The reflector and the antenna are separated from each other by a distance, d, wherein d is from about $\frac{1}{12}$ to about $\frac{1}{8}$ of a wavelength, and in certain embodiments about $\frac{1}{10}$ of a wavelength, of the electromagnetic energy emitted from the antenna.

According to another embodiment of the present invention there is provided an electrosurgical device for tissue ablation. The device comprises a microwave signal generator for generating microwave energy, a transmission line for transmitting the microwave energy from the signal generator, an antenna coupled to the transmission line and configured for emitting microwave energy therefrom sufficiently strong to cause tissue ablation, and an electrically conductive reflector positioned laterally from the antenna and configured to redirect at least a portion of the microwave energy emitted from the antenna toward a side of the device opposite the reflector. The transmission line comprises an inner conductor, an outer conductor and a first dielectric material disposed therebetween. The device further comprises a second dielectric material surrounding the antenna and disposed between the antenna and reflector. The second dielectric material has a dielectric constant that is greater than the dielectric constant of the first dielectric material. The reflector and the antenna are separated from each other by a distance, d, wherein d is from about $\frac{1}{12}$ to about $\frac{1}{8}$ of a wavelength, and in certain embodiments about $\frac{1}{10}$ of a wavelength, of the microwave energy emitted from the antenna.

DETAILED DESCRIPTION OF THE PREFERRED EMBODIMENT

FIGS. 1-4 schematically depict an electrosurgical device 10 in accordance with one embodiment of the present invention. Device 10 generally comprises a transmission line 12 that is configured for transmitting an electromagnetic signal from a signal generator, described in further detail below. As more clearly shown in FIGS. 2-4, the transmission line 12 is a coaxial cable that comprises an inner conductor 14 and an outer conductor 16 and a dielectric material 18 disposed therebetween. In certain embodiments, the inner conductor 14 comprises copper, silver, gold, silver-plated copper weld, or any combination thereof, and the outer conductor 16 comprises a conductive metal, for example, copper. In the case of a flexible device 10, outer conductor 16 may be a woven metallic (e.g., copper) shield. The dielectric material 18 may comprise, for example, polytetrafluoroethylene, air, polyethylene, alumina, nylon, and combinations thereof.

Figure 1:
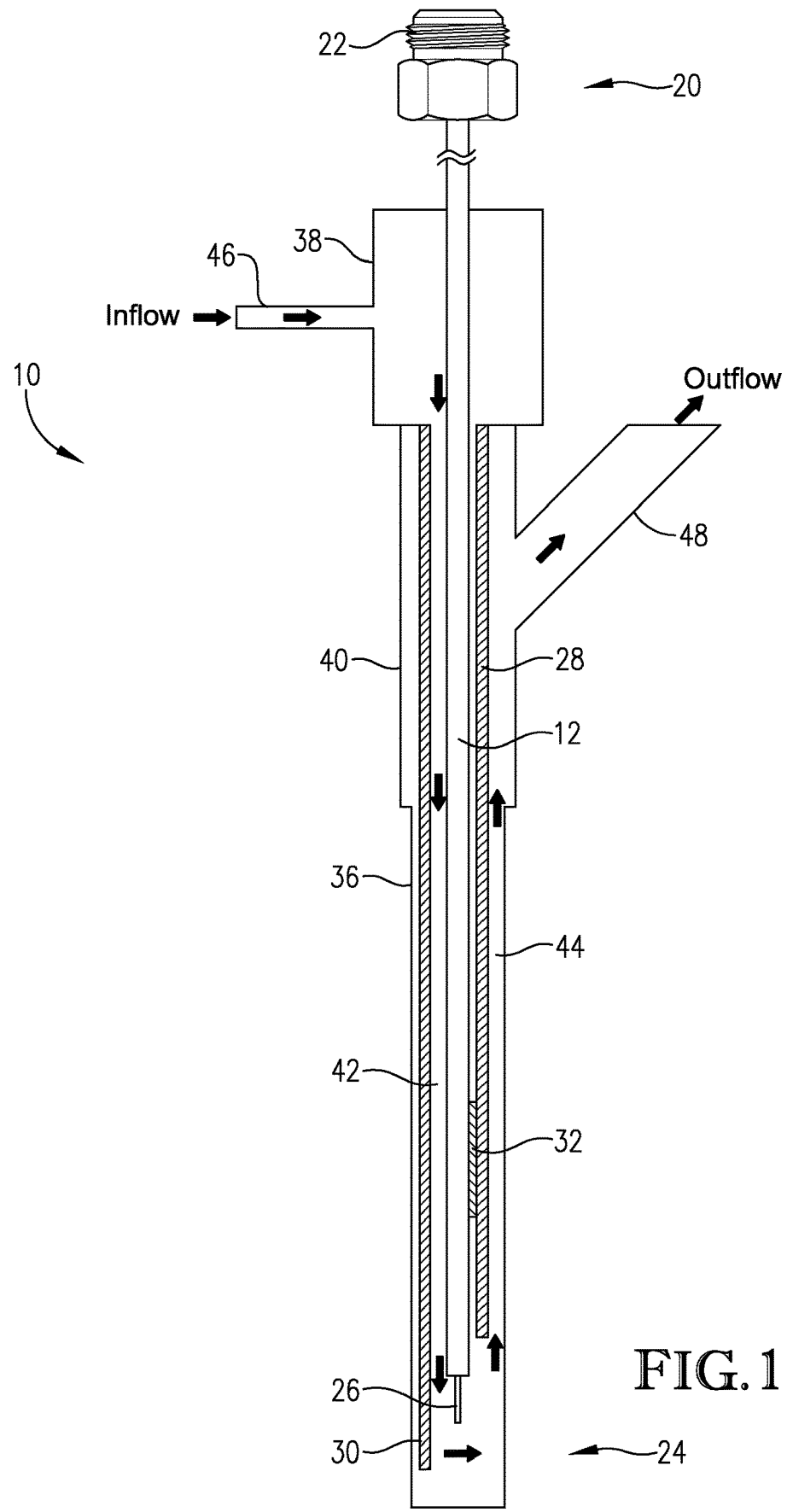
FIG. 1 is a schematic diagram of an electrosurgical device made in accordance with one embodiment of the present invention.

As shown in FIG. 1, the proximal end 20 of transmission line 12 comprises an SMA connector 22 or other structure (e.g., N-type and BNC connectors) that is suitable for connecting the transmission line to the signal generator. The distal end 24 of transmission line 12 comprises a portion of the line in which the outer conductor 16 and dielectric material 18 have been removed so as to form an antenna 26 that is operable to emit electromagnetic energy therefrom, which is sufficiently strong to cause tissue ablation. In certain embodiments, antenna 26 comprises a monopole antenna; however, other types of antenna configurations, such as dipole, slot, and helical antennas, may also be used without departing from the scope of the present invention.

Figure 2:
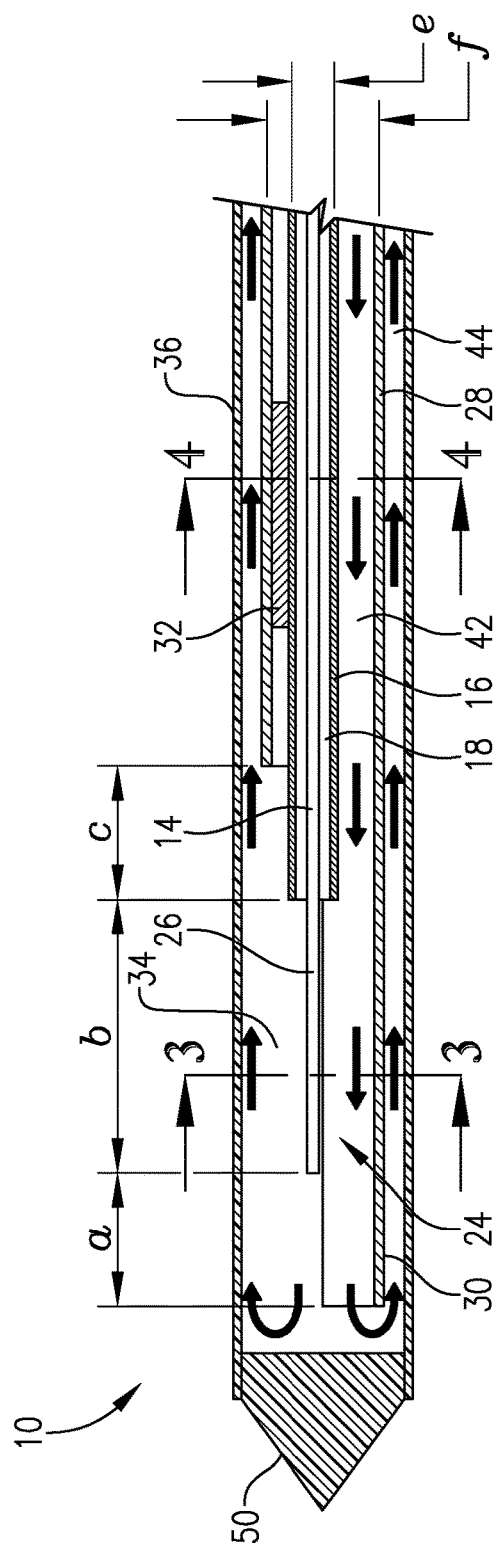
FIG. 2 is a cross-sectional view of the distal end of the electrosurgical device of FIG. 1.

The transmission line 12 is secured within an inner tubular member 28. As illustrated in FIG. 2, a portion of the distal end of tubular member 28 has been removed so as to form a hemicylindrical reflector 30. Because a portion of tubular member 28 is utilized to create reflector 30, tubular member 28 comprises an electrically-conductive material, such as stainless steel, silver, copper, gold, and other metals and alloys. In other embodiments, reflector 30 is made from any material with high electrical conductivity ($\sigma > \sim 10^4$ S/m). It is within the scope of the present invention for the reflector to comprise alternate configurations, including different shapes and to be fabricated from a material that is different than tubular member 28. For example, reflector 30 may be rectilinear as opposed to the curvilinear configuration illustrated in FIG. 3. Reflector 30 need not have a uniform cross-sectional configuration as the configuration could change along the length of the reflector.

Figure 3:
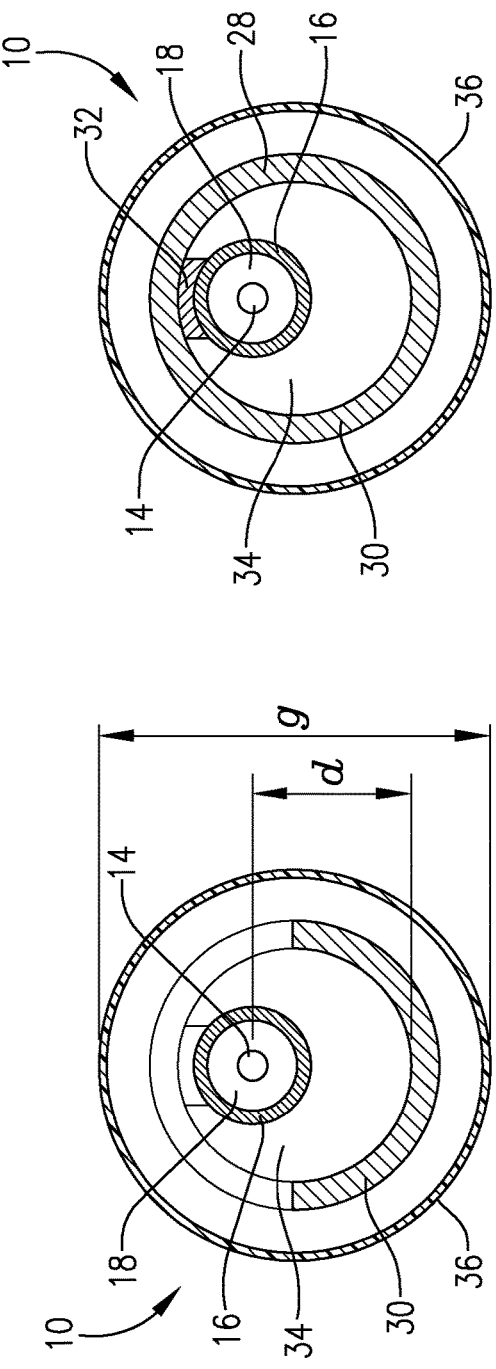
FIG. 3 is a cross-sectional view of the electrosurgical device taken along line 3-3 of FIG. 2.

In certain embodiments in which reflector 30 comprises a hemicylindrical shape, the reflector has an arc angle, θ, that is equal to 180° or less, or less than 160°, or less than 140°. In other embodiments, θ is from about 80° to about 200°, or from about 100° to about 180°, or from about 120° to about 140°. As illustrated in FIG. 3, θ is equal to approximately 180°, and is defined as the angle that an arc makes at the center of the circle of which it is a part. As discussed below, selection of θ affects the impedance matching between antenna 26 and transmission line 12 which also impacts the observed radial extent of the ablation zones in a forward direction (r), in a reverse direction (r'), and the width of the ablation zone (w).

In certain embodiments, the relative positioning of transmission line 12 (and antenna 26) within tubular member 28 is maintained by one or more brackets 32. Bracket 32 may comprise a non-conducting material so that tubular member 28 (and reflector 30) is not electrically coupled with outer conductor 16. However, it is within the scope of the present invention for bracket 32 to comprise an electrically conductive material, such as a metal. In alternate embodiments, bracket 32 need not be used. Rather, an adhesive may be used to affix transmission line 12 to the inner wall of tubular member 28.

A dielectric material 34 surrounds antenna 26 and is disposed between the antenna and reflector 30. In certain embodiments, dielectric material 34 is different than dielectric material 18 that comprises transmission line 12. In particular embodiments, dielectric material 34 has a significantly greater dielectric constant than dielectric material 18. As explained below, the selection of dielectric material 18 plays a role in the selection of a relative positioning of antenna 26 and reflector 30 (d in FIG. 3) so as to achieve an optimal impedance matching and avoid undesirable energy loss and heat generation. In certain embodiments, dielectric material 34 comprises a material selected from the group consisting of water and metal oxides, such as titanium dioxide. In other embodiments, dielectric material 34 has a relatively high dielectric constant, preferably greater than 20, greater than 50, or greater than 75. In still other embodiments, dielectric material 34 does not comprise a thermoplastic or elastomeric material such as an epoxy, polyethylene, polytetrafluoroethylene (PTFE), polyether block amide, polyetherimide, polyimide-based polymers, or a ceramic material, as these materials tend to exhibit very low dielectric constant values (e.g. PTFE has a dielectric constant of 2.1).

Device 10 further comprises an outer, non-electrically conductive tubular body 36 inside of which at least reflector 30 and the antenna 26 are received. As the microwaves emitted from antenna 26 must pass through tubular body 36 in order to reach the tissue targeted for ablation, in certain embodiments tubular body 36 comprises an elastomeric or plastic material such as polyimide, PTFE, and polyether ether ketone (PEEK) tubing. This construction, as opposed to being formed from an electrically conductive material such as metal, also reduces adhesion of ablated tissue to device 10 during use thereby facilitating easier insertion and withdrawal of the device into and from the patient's body. As illustrated in FIG. 1, tubular body 36 may be connected to a number of peripheral fittings such as a hemostasis valve 38 and Y-adapter 40 in order to circulate a cooling fluid within device 10 in order to dissipate heat that is generated during operation. Tubular body 36 may also be utilized in the formation of reflector 30. For example, instead of being an extension of tubular member 28, reflector 30 may comprise a highly conductive coating material, such as an epoxy or metallic paint, that is applied across a portion of the interior surface of the distal end of tubular body 36 at the desired arc angle. Such a configuration can be used to substantially decrease the overall diameter for device 10.

The transmission line 12 and tubular member 28 cooperate to define an innermost annular region 42 into which the cooling fluid may be directed from hemostasis valve 38 and Y-adapter 40. Tubular member 28 and tubular body 36 cooperate to define an outermost annular region 44. The innermost annular region 42 is configured to conduct a cooling fluid that is introduced into the device via an inlet 46 of hemostasis valve 38 in a first direction toward the distal end of the tubular member 28. The outermost annular region 44 is configured to conduct the cooling fluid in a second direction away from the distal end of tubular member 28 and toward an outlet 48 formed in Y-adapter 40.

The cooling fluid circulated within device 10 can be any appropriate fluid for transferring heat from the various components making up device 10. The cooling fluid cools device 10 thereby precluding thermal damage to non-targeted tissue along the length of the device. In certain embodiments water is a preferred cooling fluid. However, it is within the scope of the present invention for other cooling fluids to be used such as saline, FLUORINERT, liquid chlorodifluoromethane, nitrous oxide, nitrogen, carbon dioxide and air.

An advantage of certain embodiments of the present invention is that the cooling fluid being conducted within annular region 42 may also comprise the dielectric material 34 that surrounds antenna 26 and is located between the antenna and reflector 30. Thus, in these embodiments, the cooling fluid serves two functions: removal of undesirable heat generated during operation of device 10 and as the dielectric material 34 through which the microwave energy emitted by antenna 26 passes.

In certain embodiments of the present invention, to facilitate direct percutaneous insertion, device 10 may be equipped with a sharp, rigid catheter tip 50. In certain embodiments, tip 50 may be attached to the distal end of reflector 30. In other embodiments of the present invention, device 10 can readily be integrated with flexible coaxial cable for endoscopic, endoluminal, or endovascular targeting of structures. In such embodiments, tubular body 36 may comprise a balloon or other highly flexible and resilient structure. In certain embodiments, device 10 may be equipped with some type of steering mechanism that permits a physician to direct the distal portion of the device to a proper endoluminal location.

As noted above, impedance matching between transmission line 12 and antenna 26 can be achieved through selection of dielectric material 34 and a number of structural configurations for reflector 30 and antenna 26. It has been discovered that impedance matching between the antenna 26 and transmission line 12, as indicated by the calculated antenna reflection coefficient ($S_{11}$), can be achieved, at least in part, by selective positioning of antenna 26 and reflector 30. In particular, it has been discovered that a low antenna reflection coefficient could be achieved when the antenna-reflector spacing, d, was from about 1/12 to about 1/8 of a wavelength of the electromagnetic energy emitted from the antenna. More preferably, this distance is approximately 1/10 of a wavelength. In certain embodiments, over the frequency range 2-3 GHz, the following relationship holds between d (in mm) and wavelength λ (in mm): d=0.60λ-7.02. This distance, d, as labeled in FIG. 3 is measured from the center of the antenna to the inner wall of the reflector at its center point (e.g., in the case of a hemicylindrical reflector, the midpoint of its arc length).

The wavelength of electromagnetic energy emitted from antenna 26 is dependent, at least in part, upon the dielectric constant value of the dielectric material 34 surrounding the antenna. In certain applications, such as where device 10 will be used endovascularly or percutaneously, it can be advantageous for device 10 to be as narrow as possible. Selecting a dielectric material 34 with a high dielectric constant will produce shorter wavelengths, and hence, a smaller d value can be used and still achieve a desirable degree of impedance matching. In other applications, such as where device 10 will be used endoscopically, the device size can be greater (and have a greater d value) and thus a dielectric material 34 with a lower dielectric constant can be used. For example, in certain embodiments where a small device size is required, the dielectric material 34 may comprise a metal oxide material, which can have a dielectric constant of greater than 100 and produce very short wavelengths. In other embodiments, where a larger device size can be tolerated, the dielectric material 34 can be water, which has a dielectric constant of 78.6 at 2.45 GHz, and the device can also enjoy the benefits of water cooling as described above.

The selection of a d value can influence the structural relationship between the antenna and other parts of device 10 besides reflector 30. In certain embodiments, antenna 26 has a longitudinal axis that is offset from, but parallel to, the longitudinal axis of device 10. This offset may be in a direction towards or away from reflector 30. In other embodiments, the longitudinal axis of antenna 26 may be coaxial with the longitudinal axis of device 10. In still other embodiments, the longitudinal axis of antenna 26 may be transverse to the longitudinal axis of device 10. In certain embodiments in which antenna 26 is formed from the inner conductor 14 of transmission line 12, the antenna can be bent out of coaxial alignment with the inner conductor to achieve the desired d value. This structural relationship between antenna 26 and various portions of device 10 is also another variable that can be used to achieve the desired impedance matching between the antenna and transmission line 12.

Figure 6:
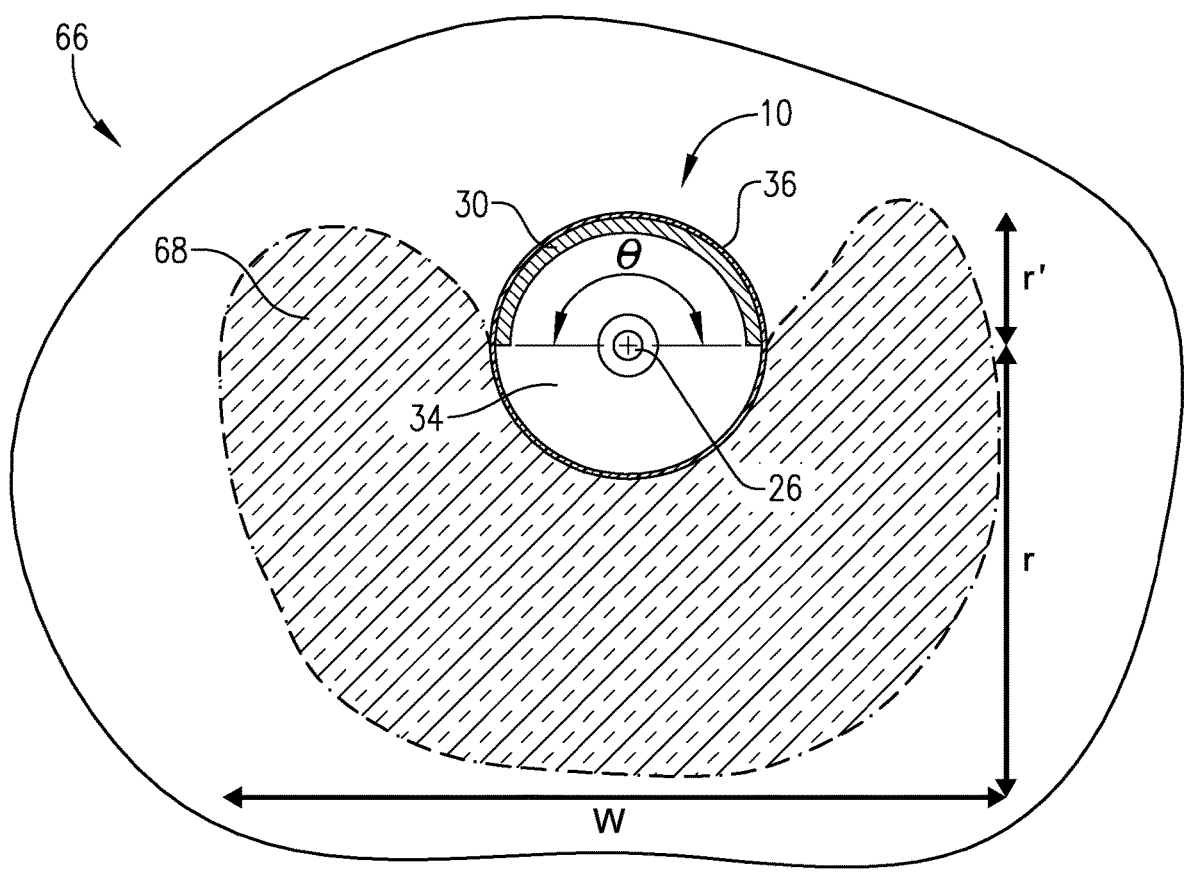
FIG. 6 is a representation of an exemplary ablation pattern produced with a device according to one embodiment of the present invention taken perpendicular to the longitudinal axis of the electrosurgical device.

It has been discovered that the arc angle, θ, of the reflector 30 can also have an effect on the antenna reflection coefficient ($S_{11}$) and the extents of the ablation zone, characterized by the dimensions r (radial extent of the ablation zone in the forward direction), r' (radial extent of the ablation zone in the reverse direction), and w (width of the ablation zone), as shown in FIG. 6. In certain embodiments, it is desirable to select θ to as to provide a low $S_{11}$ value, but also to minimize r' so as to avoid damage to non-targeted tissue. In other embodiments, it may be desirable to select θ so as to provide a low $S_{11}$ value, but maximize r so as to provide as deep of an ablation zone into the targeted tissue as possible. These concepts are illustrated in the Examples below.

Because effective impedance matching between the antenna 26 and transmission line 12 can be achieved through the control of a number of structural variables, such as dielectric material 34 selection, θ, and d, device 10 can be constructed without using an impedance matching device between transmission line 12 and antenna 26. Common impedance matching devices used to place the antenna structure in resonance increase the efficiency thereof include capacitors, resistors, inductors, stub tuners, stub transmission lines, or any combination thereof, whether in series or in parallel with the antenna.

Figure 5:
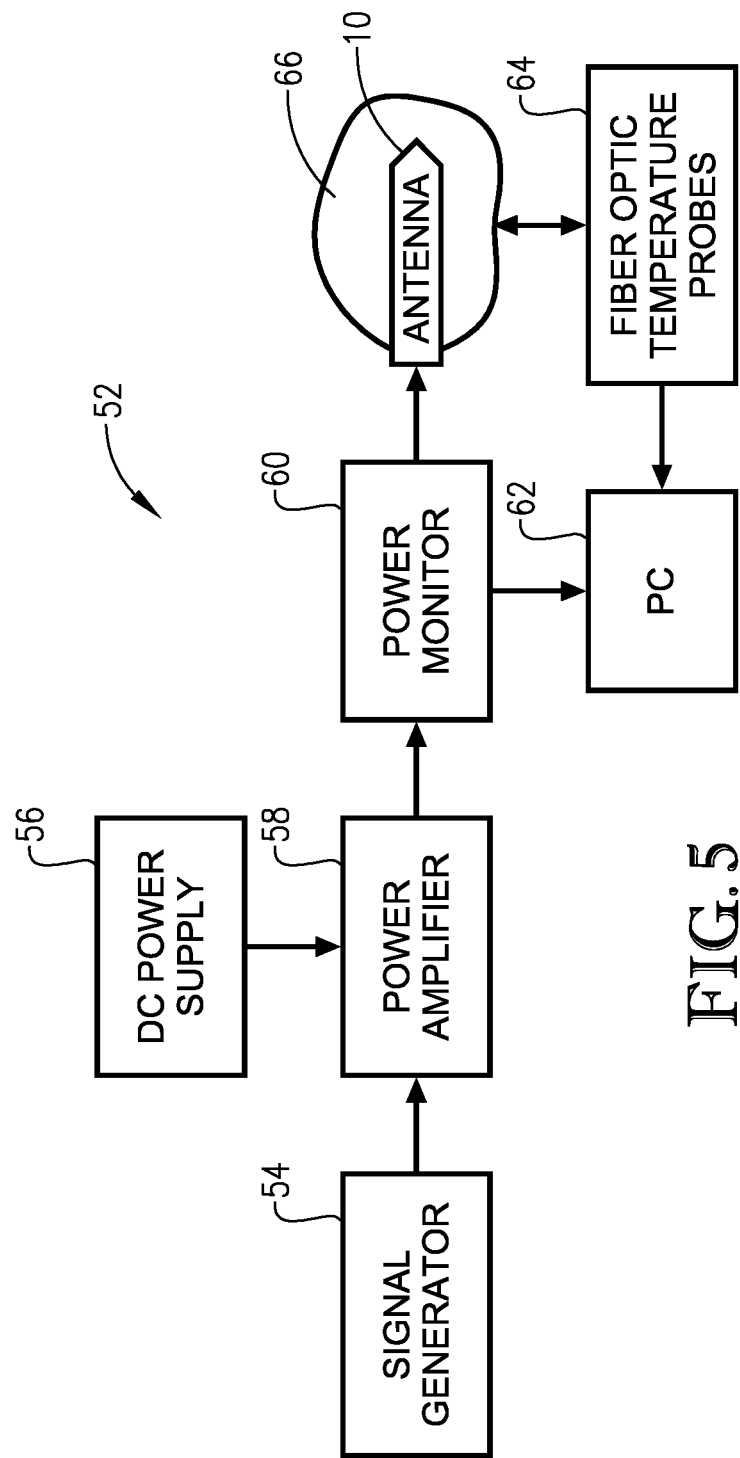
FIG. 5 is a schematic diagram of an embodiment of an electrosurgical device including a power supply, signal generator and antenna.

FIG. 5 schematically depicts an exemplary electrosurgical device 10 constructed in accordance with one embodiment of the present invention. An electromagnetic power source 52 is used to generate and transmit the desired microwave energy to device 10. Electromagnetic power source 52 may include a microwave signal generator 54, and optionally a DC power supply 56, a power amplifier 58, and a power monitor 60. The operation of device 10 and the various pieces of equipment utilized by power source 52 may be monitored and controlled by a microprocessor 62, such as a personal computer or a handheld device. In certain embodiments, the frequencies generated by the signal generator are similar to those that are associated with the frequencies typically used to heat water. In particular embodiments, the frequencies generated range from about 800 MHz to 6 GHz, from about 900 MHz to about 5 GHz, or from about 1 GHz to about 3 GHz. In preferred embodiments, particularly for devices used for experimental clinical work, the frequencies generated are 915 MHz or 2.45 GHz. Optionally, temperature probes 64 can be inserted into the tissue 66 along with device 10 so as to monitor the temperature of tissue being ablated and adjacent to the tissue being ablated.

As described above, antenna 26 is designed to have an impedance close to that of the transmission line 12 from signal generator 54 (nominally, 50Ω) at the operating frequency. The impedance presented by antenna 26 is a function of the dimensions of the antenna as well as the wavelength at the operating frequency. Because of this impedance matching, device 10 can be used in methods of treating body tissues that are in close proximity to critical structures. Device 10 is configured to emit microwave energy toward the targeted tissue with a directional radiation pattern. The physician or operator of device 10 may orient the device such that energy is emitted substantially toward the target structure and away from the critical tissues that should not be damaged. In such applications, a physician may orient the antenna towards the target structure, and away from the critical tissues that should not be damaged. Device 10 can be applied to target tumors in regions that can be accessed percutaneously, endoluminally (e.g., bronchii, urethra, rectum, stomach, esophagus) or endovascularly (e.g., renal nerves). Device 10 may also be used for moderate heating of tissues (e.g., between about 41 and 44° C.) as an adjuvant to radiation and or chemotherapy for treatment of select cancers.

Device 10 can be used in connection with sensing or imaging equipment configured to give real-time feedback to the physician conducting a procedure. In certain embodiments, the sensing or imaging equipment can give the physician information regarding the ablation boundary associated with the use of device 10. If the ablation boundary does not extend to the edge of the desired target, the physician can rotate device 10 to treat the full extent of tissue in between the desired margins. For example, device 10 can be fabricated from MRI-compatible materials for use under MRI guidance. Such devices do not generate a visible imaging artifact when introduced into an MRI bore. Use of device 10 with an MRI offers the benefit of real-time volumetric temperature imaging for feedback controlled procedures. For instance, when targeting structures in very close proximity to several critical structures, MRI temperature imaging could be used to assess when the treatment boundary extended to the edge of the desired target, and then guide rotation of the device to target tissue in another direction.

EXAMPLES

The following examples set forth exemplary electrosurgical devices constructed in accordance with certain embodiments of the present invention, and report the data generated during the use of such devices. It is to be understood, however, that these examples are provided by way of illustration and nothing therein should be taken as a limitation upon the overall scope of the invention.

Example 1

Electrosurgical Device for Creating Directional Microwave Ablation Zones

An electrosurgical device with a directional radiation pattern was fabricated as follows. A UT-47 semi-rigid coaxial cable with a length of about 80 mm had one end (proximal end) electrically coupled to a female sub-miniature A (SMA) adapter. The coaxial cable comprises a central conductor, enclosed by a dielectric (i.e. electrically insulating) layer, which is in turn encompassed by an outer conductor. The inner conductor was made of silver-plated copper weld (SPCW), the dielectric was PTFE (polytetrafluoroethylene, trade name TEFLON), and the outer conductor was copper. The distal end of the coaxial cable had the outer conductor and dielectric material removed to expose the inner conductor by a length of about 6 mm (dimension b of FIG. 2), thereby forming a monopole radiator. As illustrated in FIG. 3, the UT-47 coaxial cable was placed asymmetrically into a stainless steel tube with an outer diameter of 3 mm (dimension f of FIG. 2), inner diameter of 2.5 mm, and a length of 83 mm. The distance from the tip of the monopole to the inner wall of the reflector (d) was 1.5 mm.

A portion of the stainless steel tubing was removed at the distal end of the structure to form a reflector. The angular extent over which the reflector enclosed the antenna affects the shape and size of the radiation pattern and how directional the energy deposition was. Furthermore, a precisely machined plastic bracket, 1 mm thick and a length of 10 mm was fabricated with a 3D printer, and was used to position and support the antenna in its optimal position. Water cooling was implemented in the device by adding a hemostasis valve below the SMA connector and above the stainless steel tube, as depicted in FIG. 1. A Y-adapter was then connected to the hemostasis valve with the stainless steel tube extending out from the bottom of the adapter.

The stainless steel tubing separated the inflow from the hemostasis valve and outflow from the Y-adapter. A waterproof seal was made in between the stainless tubing and the hemostasis valve using LOCTITE 4013 adhesive, ensuring proper water flow. Next, polyimide tubing with an outer diameter of 3.98 mm and inner diameter of 3.85 mm was placed over the stainless tubing and antenna. LOCTITE 4013 adhesive was also used to make a water proof seal between the polyimide tubing and the bottom of the Y-adapter. The open tip of the polyimide tubing was sealed using J-B Weld Adhesive.

Example 2

Electrosurgical Device for Creating Directional Microwave Ablation Zones

In this example, the four geometric parameters a, b, c, and d from FIG. 2, along with θ (FIG. 6) were varied to minimize the antenna reflection coefficient (S11). In order to keep d practically small while maintaining low $S_{11}$, a material with high dielectric constant (water, εr=78.6 at 2.45 GHz) was employed. UT-47 coaxial cable (151-0002, Micro-coax, Philadelphia, Pa., USA) was employed to implement the monopole antenna. The UT-47 cable was inserted into a 2.4-mm (OD) stainless steel tubing (McMaster-Carr, Elmhurst, Ill., USA), which served as the reflector structure. Using a custom 3-D printed bracket, the monopole was set in its optimized location. The stainless steel tube has one end secured with adhesive to a hemostasis valve (Qosina, Edgewood, N.Y., USA) to create the inflow port for water. The other end of the tube had a section of the metal removed in the desired direction of radiation. A Y-adapter (Qosina, Edgewood, N.Y., USA) was connected to the hemostasis valve to act as the outflow port for water cooling. A 3.5-mm (OD) polyimide catheter (American Durafilm, Holliston, Mass., USA) was placed over the stainless steel tube and connected with adhesive to one end of the Y-adapter. The distal end of the polyimide catheter was sealed with epoxy.

Figure 4:
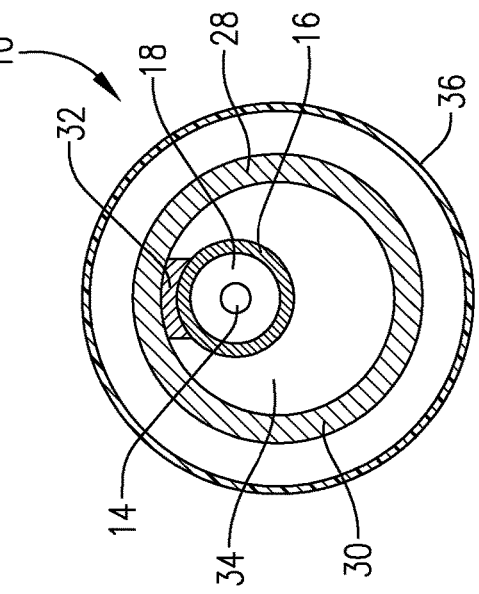
FIG. 4 is a cross-sectional view of the electrosurgical device taken along line 4-4 of FIG. 2.

A 3-D commercial FEM solver (COMSOL Multiphysics v4.4, COMSOL, Inc., Burlington, Mass., USA) was used to model electromagnetic energy radiation and subsequent heating from the directional applicator with the geometry shown in FIGS. 2-4. The model was employed to solve the Helmholtz electromagnetic wave equation $$\nabla^2 E - k_0^2 \left( \varepsilon_r - \frac{j\sigma}{\omega \varepsilon_0} \right) E = 0$$

where E [V/m] is the electric field, $k_0$ [m$^{-1}$] is the free-space wavenumber, $\varepsilon_r$ is the relative permittivity, σ [S/m] is the effective electrical conductivity, ω [rads/s] is the angular frequency, and $\varepsilon_0$ [F/m] is the permittivity of free-space. An 80-mm long antenna placed at the center of 80-mm diameter cylinder with properties of liver tissue was modeled. Table 1 lists the electromagnetic properties of all materials used in our simulations at 2.45 GHz.

TABLE 1

| Material | Permittivity, $\varepsilon_r$ | Conductivity, σ [S/m] |
| --- | --- | --- |
| Liver | 43 | 1.69 |
| Water | 78.6 | 1.45 |
| PTFE | 2.03 | 0 |
| Polyimide Tubing | 3.4 | 0 |

A scattering boundary condition was applied to the outer surface of the simulated liver region to minimize reflection of incident EM waves. All metallic regions were modeled as perfect electric conductors implying σ→∞. A coaxial port boundary condition was applied on the surface of the dielectric material of the coaxial line on the top of the cylinder to specify the desired forward power. A nonuniform mesh of tetrahedral elements was applied with finest mesh at the antenna feed boundary (maximum edge length 0.005 mm) and relatively coarser mesh in liver tissue furthest away from the antenna (maximum edge length 4 mm). This mesh resolution was determined following iterative adjustments to satisfy a Cauchy convergence test on the $S_{11}$, $$|S'_{11} - S_{11}| \leq 0.1 \text{ dB}$$

where $S'_{11}$ is the result of a coarser mesh and $S_{11}$ is the result of the original mesh. The complete mesh consisted of approximately 400 000 elements. Simulations were run on a 12 core Pentium processor with 64-GB RAM operating Red Hat Linux. A single simulation took approximately 40 min to complete.

Parametric sweeps were used to optimize the antenna dimensions with the objective of minimizing the antenna reflection coefficient at 2.45 GHz. The parameters a, b, and c were varied from 1 to 10 mm in 1-mm increments, while parameter d was varied from 2.5 to 4 mm in 0.25-mm increments. Following the optimization process, a frequency sweep was performed from 2 to 3 GHz in 100 MHz steps to characterize the frequency response of the antenna. The power deposited by the antenna into the tissue was calculated using $$Q = J \cdot E$$

where Q [W/m$^3$] is the volumetric power deposition, J [A/m$^2$] is the current density, and E [V/m] is the electric field intensity. A heat transfer model was employed to solve Pennes' bioheat equation $$\rho c_l \frac{\partial T}{\partial t} = \nabla \cdot (k \nabla T) + Q - \dot{m}_{bl} c_{bl} (T - T_b)$$

where ρ is the density of liver (1050 kg/m$^3$), $c_l$ is the heat capacity of liver at constant pressure (3600 J/kg/K), k is the thermal conductivity of liver (0.51 W/m/K), QW/m$^3$ [J] is the energy deposited into the liver defined by (3), $\dot{m}_{bl}$ [kg/(m$^3$ s)] is the blood mass perfusion rate, $c_{bl}$ is the heat capacity of blood at constant pressure (3600 J/kg/K), and $T_b$ is the temperature of blood (37° C.). Thermal insulation boundary conditions were applied at the outer extents of the computational domain. To approximate catheter cooling, a fixed temperature boundary condition (20° C.) was applied on the catheter surface. The 52° C. isotherm was used to approximate extents of ablation zone following 10-min ablations in ex vivo tissue. Perfusion values of 0 (ex vivo tissue), 3 (low perfusion tissues such as prostate), and 10 kg/m$^3$/s (high perfusion tissues such as the kidney and liver) were considered. For all in vivo simulations, blood perfusion was reduced to 0 kg/m$^3$/s at tissue temperatures in excess of 60° C. to approximate the effects of microvascular stasis. Estimates of the ablation zone for in vivo simulations were determined using an Arrhenius model $$\Omega(\tau) = \int_0^\tau A e^{\left[\frac{-E_a}{RT(t)}\right]} dt.$$

For in vivo simulations, the region of ablation was approximated with the Ω=1 threshold after 10 min of heating. FIG. 6 illustrates the dimensions of the ablation zone 68 within a tissue sample 66 assessed to evaluate the directionality of candidate antenna designs. For nominal antenna designs, the reflector geometry was a half cylinder (θ=180°). Further simulations were performed varying θ from 20° to 220° in 20° increments. The extents of the ablation zone were characterized by the dimensions r (radial extent of the ablation zone in the forward direction), r' (radial extent of the ablation zone in the reverse direction), and w (width of the ablation zone). Applied power levels of 50 and 80 W, 10-min heating durations were considered. Simulations were employed to determine the impact of the reflector enclosure around the antenna on the reflection coefficient and heating pattern.

The broadband reflection coefficient for fabricated antennas was measured using an HP 8753D vector network analyzer. Measurements were conducted with room temperature circulating tap water with the antenna inserted to a depth of at least 50 mm in ex vivo porcine muscle. Heating experiments in ex vivo porcine tissue were performed with an input power of 50 and 80 W using the fabricated antennas to compare to simulation. Porcine muscle samples, enclosed within water-sealed bags, were heated to ~30° C. in a temperature controlled water bath. Fiber optic temperature probes (Neoptix RFX-04-1, Canada) were placed into the porcine tissue. Room temperature tap water was circulated through the antenna at a flow rate of 5 ml/s with a peristaltic pump (Cole-Parmer, 7554-90, Vernon Hills, Ill., USA). Five experimental ablations were performed for each input power of 50 and 80 W applied for 10 min. Following ablations, tissue samples were sliced perpendicular to the length of the antenna at the depth that was approximately the position of the tip of the monopole to measure and photograph the area of tissue ablation.

Figure 7:
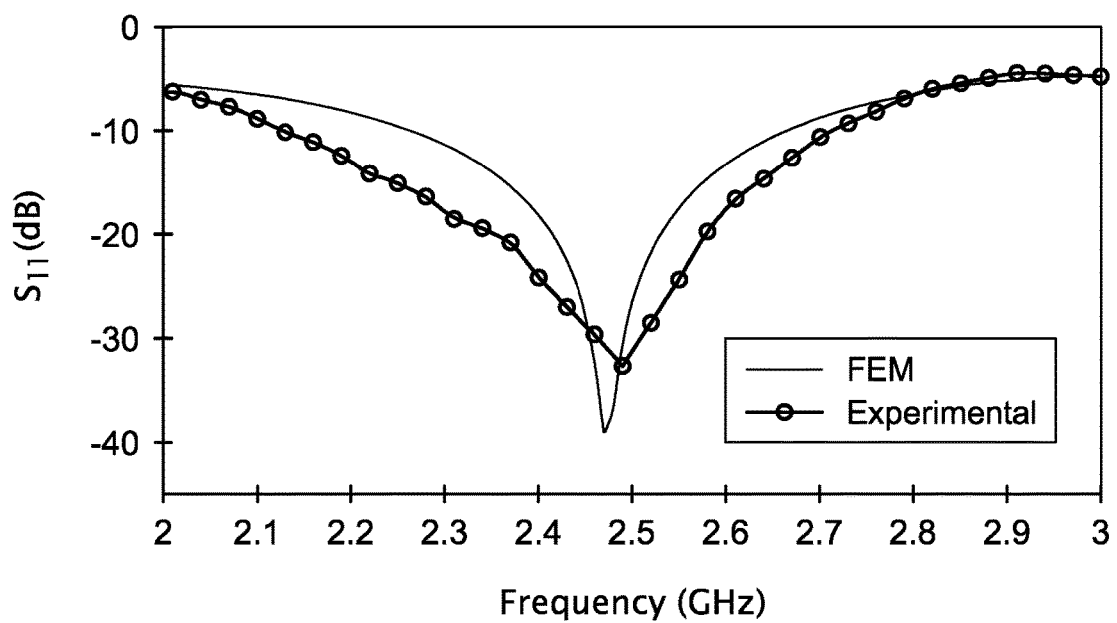
FIG. 7 is a chart illustrating simulated and measured reflection coefficient of an antenna design according to one embodiment of the present invention.

FIG. 7 illustrates simulated and measured reflection coefficient of the optimized antenna design. Simulations determined the optimized values at 2.45 GHz for the antenna dimensions a, b, c, and d, to be 3 mm, 6 mm, 3 mm, and 1.2 mm, respectively. Values for e (UT-47 coaxial cable OD), f (reflector tubing OD), and g (polyimide tubing OD) were 2.2 mm, 2.4 mm, and 3.5 mm, respectively.

Simulations indicated a minimum $S_{11}$ of −39 dB at 2.47 GHz with a −15 dB bandwidth of 210 MHz. Measurements with fabricated antennas indicated a minimum $S_{11}$ of −32.6 dB at 2.49 GHz with a −15 dB bandwidth of 390 MHz. Simulations indicated $S_{11}$ at 2.45 GHz remained under −20 dB for insertion depths ranging from 3-8 cm.

Figure 8A:
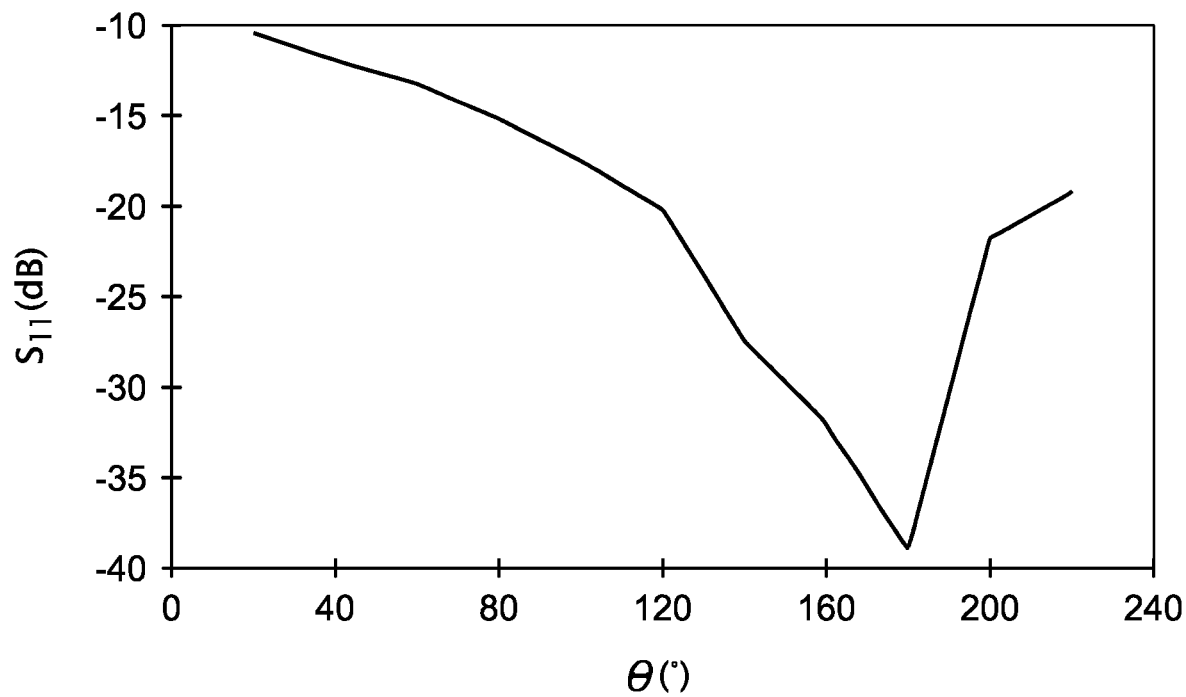
FIG. 8a depicts changes in $S_{11}$ for varying reflector geometries (θ)
Figure 8B:
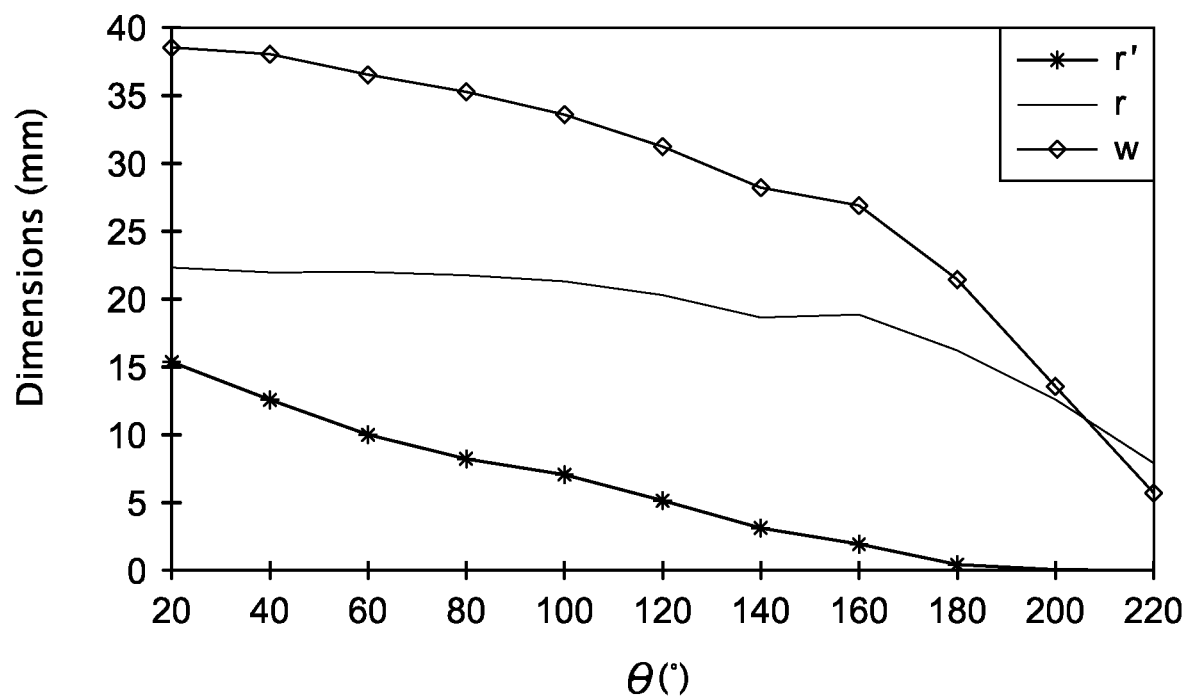
FIG. 8b depicts changes in the extent of ablation zones for varying reflector geometries (θ)

FIGS. 8a and 8b depict changes in $S_{11}$, and extents of the ablation zone for varying reflector geometries (θ).

These simulations indicate that θ can be selected to trade off reflection coefficient, width of the ablation zone, depth of forward heating, and extent of backward heating.

Ex vivo heating experiments were performed in porcine tissue using two antennas, with θ=180° and θ=140°, respectively. 180° was chosen as it was the design with minimal $S_{11}$ and 140° was chosen since it was the shallowest reflector design (smallest θ) with an $S_{11}$ below −20 dB. Table 2 lists the dimensions (mean and standard deviation) r, r', and w of the observed ablation zones from slices taken orthogonally for 5 trials.

TABLE 2

| | θ [°] | | |
|---|---|---|---|
| | 180 | 180 | 140 |
| | Input Power [W] | | |
| | 50 | 80 | 80 |
| Experimental r [mm] | 13.4 ± 1 | 15.4 ± 0.5 | 17.6 ± 0.5 |
| Simulated r [mm] | 13 | 17.25 | 21.25 |
| Experimental r' [mm] | 1 ± 0.5 | 2.3 ± 0.5 | 5.2 ± 2 |
| Simulated r' [mm] | 0 | 0.5 | 5 |
| Experimental w [mm] | 22.2 ± 1.3 | 21.0 ± 0.6 | 28 ± 0.4 |
| Simulated w [mm] | 15.25 | 23.5 | 32.5 |

Figure 9:
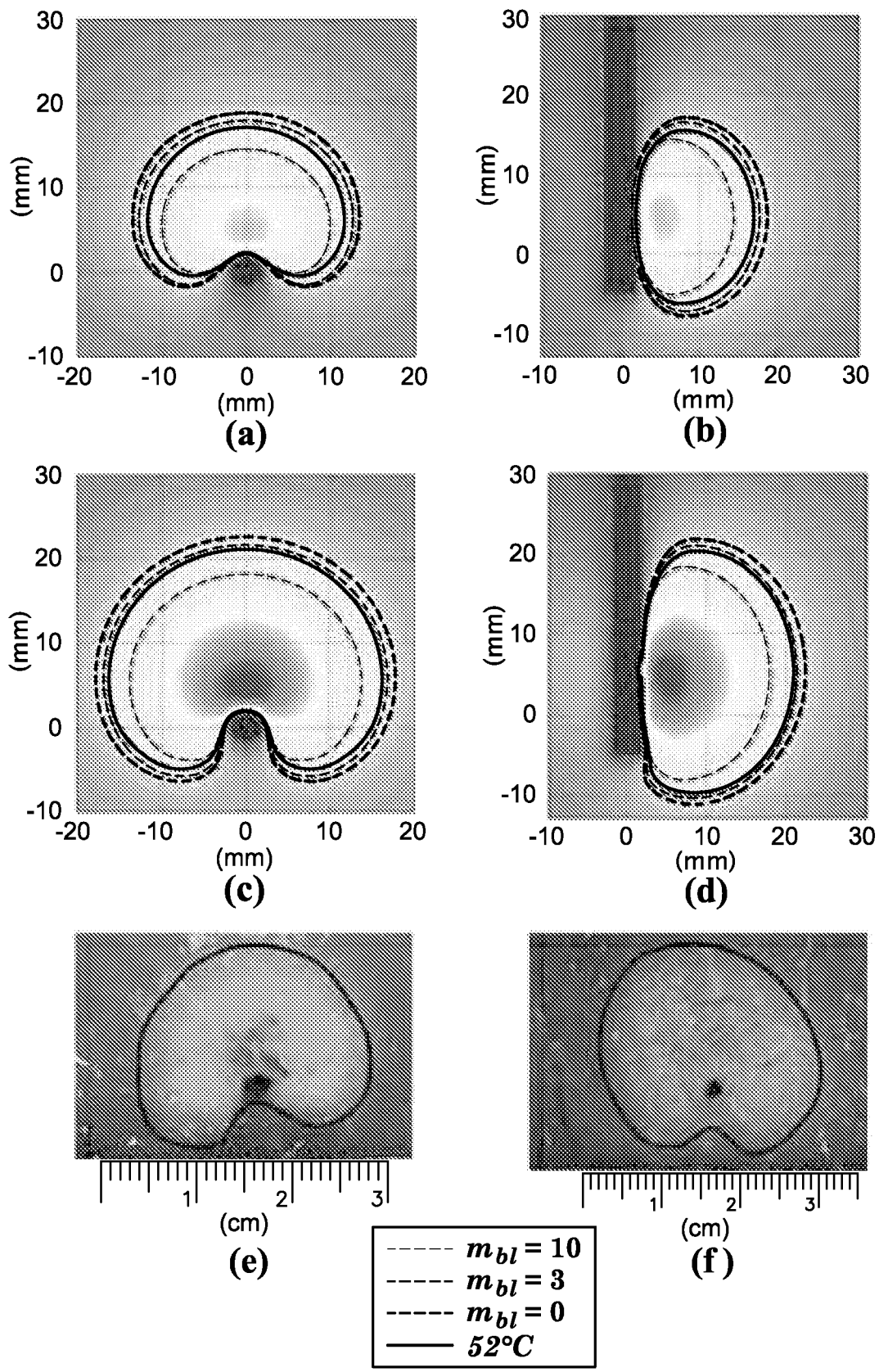
FIGS. 9(a)-(f) show representative experimental ablation zones as well as the corresponding simulated power deposition profiles for each configuration (FIGS. 9(a)-(d))

Experimental values were found to be slightly less than simulated values, with the largest measured difference of 4 mm in w in the trials using a 180° antenna with an input power of 80 W. FIG. 9 shows representative experimental ablation zones as well as the corresponding simulated power deposition profiles for each configuration. FIGS. 9(a) and 9(c) show ablation zones in a transverse plane for 180° and 140° antennas, respectively. FIGS. 9(b) and 9(d) show ablation zones in plane parallel to the antenna's longitudinal axis for 180° and 140° antennas, respectively. FIGS. 9(e) and 9(f) are photographs of observed oblation zones after 80 W heating for 10 minutes for 180° and 140° antennas, respectively.

Figure 10:
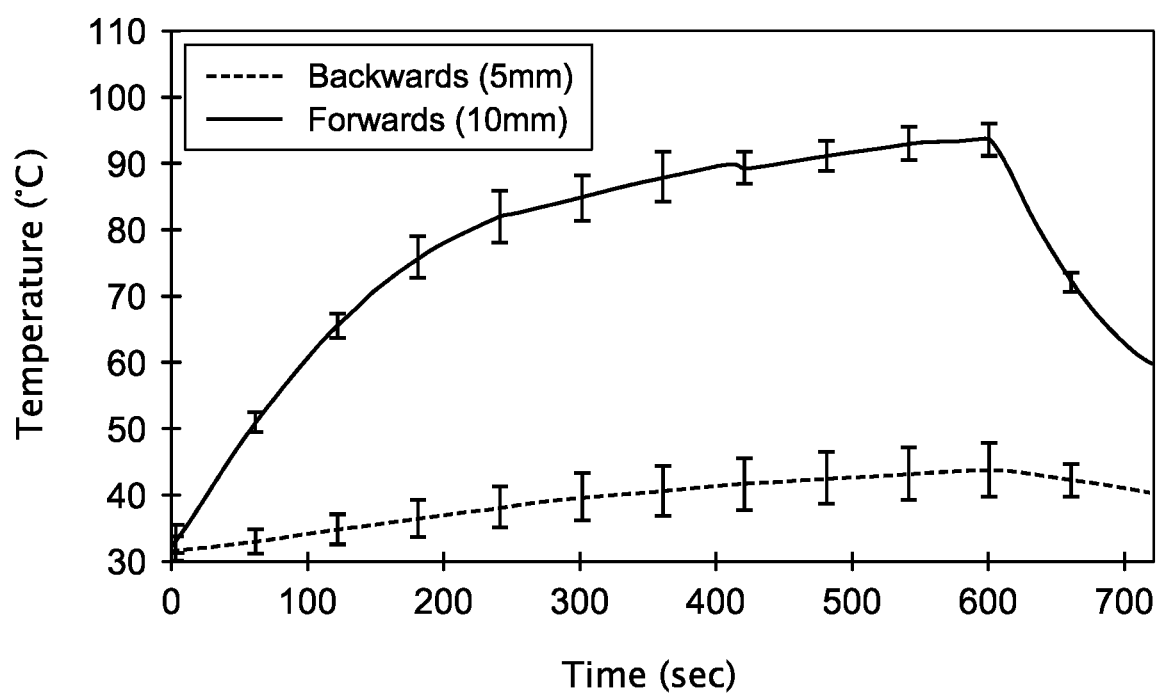
FIG. 10 shows a representative experimentally measured transient temperature profile in the forward and reverse directions during ablation with a 140° antenna.

FIG. 10 shows a representative experimentally measured transient temperature profile in the forward and reverse directions during ablation with a 140° antenna. Input power was set to 80 W for 10 mins. An increase of 61.8±2.5° C. was observed 10 mm radially in the forward direction compared to an increase of 11.1±4° C. 5 mm radially in the reverse direction.

The observed shapes of experimental ablation zones were in good agreement with patterns predicted by models. For the 180° antenna, increasing applied power from 50 to 80 W, yielded on average a 2 mm increase in radial extent of the ablation zone in good agreement with model predictions (4.25 mm increase predicted by simulations). However, no changes in width of experimental ablation zones were observed. Both models (4 mm) and experiments (2.2 mm) indicated increases in r for the 140° antenna compared to the 180° antenna. Ablation zones with the 140° antenna exhibited minimal charring of tissue. All experimental ablation zones with the 180° indicated charred tissue in the forward tissue. These observations support the hypothesis that increasing θ leads to more focused heating, while decreasing θ leads to larger ablation zones at the expense of greater reverse heating. Temperature measurements during ex vivo ablations for a 140° further demonstrated directionality of heating. Peak temperature rise 10 mm in the forward direction on average reached 93.7°±2.5° C. compared to ~11.1±4° C. observed 5 mm in the reverse direction.

We claim:

1. An electrosurgical device for tissue ablation comprising:
   a transmission line for transmitting an electromagnetic signal from a signal generator, the transmission line comprising a coaxial cable having an inner conductor, an outer conductor and a dielectric material disposed therebetween;
   an antenna coupled to the transmission line and configured for emitting electromagnetic energy therefrom sufficiently strong to cause tissue ablation, the antenna having a longitudinal axis;
   a metallic tubular member inside of which at least a portion of the transmission line is received, the metallic tubular member having a constant radius of curvature along the entire length thereof;
   a reflector positioned laterally from the antenna, the reflector comprising a forward surface facing the antenna and a rearward surface facing away from the antenna, the reflector comprising a distal end of the metallic tubular member, the reflector having a constant radius of curvature along the entire length of the antenna;
   a cooling fluid having a dielectric constant of greater than 20; and
   first and second annular regions configured to circulate the cooling fluid within the device, wherein the metallic tubular member comprising the reflector defines, at least in part, the first and second annular regions,
   the first and second annular regions being fluidly connected with a space between the reflector and the antenna to permit circulation of the cooling fluid through the space, the first and second annular regions being configured to direct a flow of the cooling fluid across both the forward and rearward surfaces of the reflector.

2. The electrosurgical device of claim 1, wherein the antenna comprises a distal portion of the coaxial cable in which the outer conductor and the dielectric material have been stripped away.

3. The electrosurgical device of claim 1, wherein the electrosurgical device does not include an impedance matching device disposed between the transmission line and the antenna.

4. The electrosurgical device of claim 1, wherein the reflector comprises a hemicylindrical shape having an arc angle, $\theta$, that is less than 180°, wherein the reflector and the antenna are separated from each other by a distance, d, wherein d is from about $1/12$ to about $1/8$ of a wavelength of the electromagnetic energy emitted from the antenna.

5. The electrosurgical device of claim 4, wherein the values of d and $\theta$ are selected to provide impedance matching between the transmission line and the antenna.

6. The electrosurgical device of claim 1, wherein the antenna comprises a monopole antenna.

7. The electrosurgical device of claim 1, wherein the longitudinal axis of the antenna is offset from the longitudinal axis of the device.

8. The electrosurgical device of claim 1, wherein the reflector comprises a hemicylindrical section of the tubular member.

9. The electrosurgical device of claim 8, wherein the device further comprises an outer, non-electrically conductive tubular body inside of which at least the reflector and the antenna are received.

10. The electrosurgical device of claim 9, wherein the transmission line and tubular member cooperate to define the first annular region, and wherein the tubular member and tubular body cooperate to define the second annular region.

11. The electrosurgical device of claim 10, wherein the first annular region is configured to conduct the cooling fluid in a first direction toward the distal end of the tubular member, and wherein the second annular region is configured to conduct the cooling fluid in a second direction away from the distal end of the tubular member.

12. The electrosurgical device of claim 11, wherein the cooling fluid is water.

13. The electrosurgical device of claim 1, wherein the cooling fluid has a dielectric constant that is greater than the dielectric constant of the dielectric material.

14. The electrosurgical device of claim 1, wherein the reflector and the antenna are separated from each other by a distance, d, wherein d is from about $1/12$ to about $1/8$ of a wavelength of the electromagnetic energy emitted from the antenna.

15. An electrosurgical device for tissue ablation comprising:
a transmission line for transmitting an electromagnetic signal from a signal generator, the transmission line comprising an inner conductor, an outer conductor, and a dielectric material disposed therebetween;
a metallic tubular member within which at least a portion of the transmission line is located, a distal end of the metallic tubular member being configured to form a reflector;
an outer tubular body inside of which the metallic tubular member and transmission line are located, the outer tubular body and the metallic tubular member comprising the reflector cooperating to define a first annular region therebetween, the metallic tubular member and the transmission line cooperating to define a second annular region therebetween, the first and second annular regions being in fluid communication and operable to circulate an aqueous cooling fluid through the device;
an antenna coupled to the transmission line and configured for emitting electromagnetic energy therefrom sufficiently strong to cause tissue ablation, the antenna having a longitudinal axis; and
wherein the electrosurgical device is of unitary construction in which the position of the transmission line is fixed relative to the metallic tubular member, and the position of the metallic tubular member is fixed relative to the outer tubular body.

16. The electrosurgical device of claim 15, wherein the reflector and the antenna are separated from each other by a distance, d, wherein d is from about $1/12$ to about $1/8$ of a wavelength of the electromagnetic energy emitted from the antenna.

17. The electrosurgical device of claim 15, wherein the metallic tubular member has a constant radius of curvature along the entire length thereof.

* * * * *